(12) United States Patent
Ladebeck

(10) Patent No.: US 7,465,839 B2
(45) Date of Patent: Dec. 16, 2008

(54) METHOD FOR THE HYDROGENATION OF KETONES

(75) Inventor: Jürgen Ladebeck, Louisville, KY (US)

(73) Assignee: Süd-Chemie AG, Munich (DE)

( * ) Notice: Subject to any disclaimer, the term of this patent is extended or adjusted under 35 U.S.C. 154(b) by 0 days.

(21) Appl. No.: 11/718,356

(22) PCT Filed: Nov. 16, 2005

(86) PCT No.: PCT/EP2005/012294

§ 371 (c)(1),
(2), (4) Date: May 1, 2007

(87) PCT Pub. No.: WO2006/053735

PCT Pub. Date: May 26, 2006

(65) Prior Publication Data

US 2008/0103338 A1    May 1, 2008

(30) Foreign Application Priority Data

Nov. 16, 2004  (DE) .................. 10 2004 055 189

(51) Int. Cl.
*C07C 27/04* (2006.01)
*C07C 29/143* (2006.01)
(52) U.S. Cl. ...................................................... 568/814
(58) Field of Classification Search .................. 568/814
See application file for complete search history.

(56) References Cited

U.S. PATENT DOCUMENTS 3,950,427 A * 4/1976 Engel et al. .................. 568/325
4,255,599 A * 3/1981 Wu et al. ..................... 585/319
5,124,295 A   6/1992 Nebesh

FOREIGN PATENT DOCUMENTS

GB      587181      4/1947

OTHER PUBLICATIONS

Nightingale, D., et al., "The Hydrogenation of Aromatic Ketones With Hydrogen and Copper-Chromium Oxide Catalyst", Journal of Organic Chemistry, 1949, pp. 1089-1093.

* cited by examiner

*Primary Examiner*—Sikarl A Witherspoon
(74) *Attorney, Agent, or Firm*—Scott R. Cox

(57) ABSTRACT

The invention relates to a process for hydrogenating ketones, wherein the ketone is fed in a mixture with hydrogen to a catalyst bed which comprises a copper chromite catalyst which has a proportion of $SiO_2$ as catalyst.

11 Claims, 8 Drawing Sheets

METHOD FOR THE HYDROGENATION OF KETONES

DESCRIPTION

Figure 1:
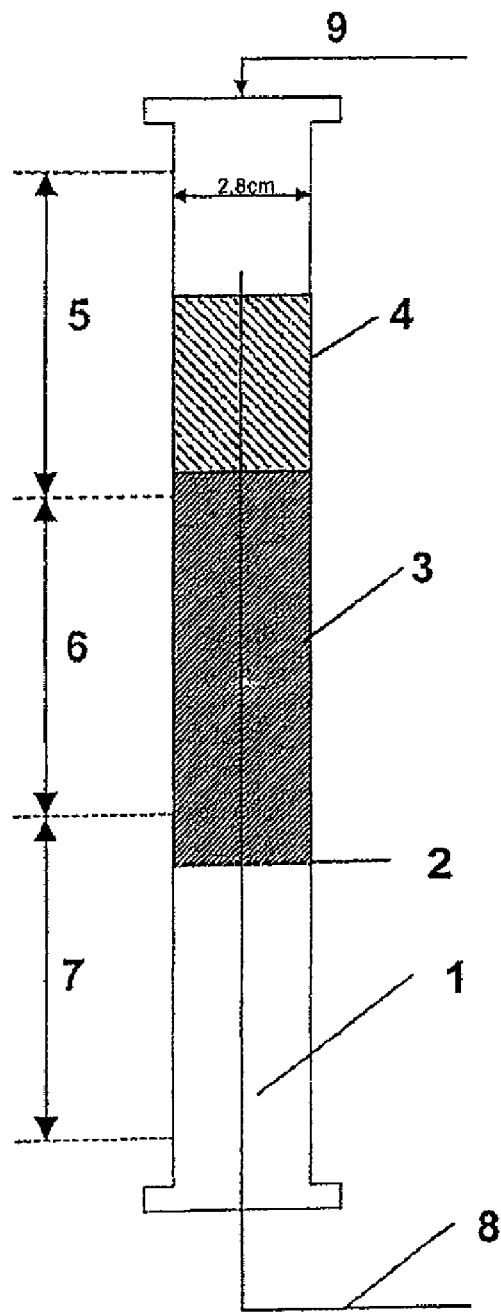

The invention relates to a process for hydrogenating ketones.

The hydrogenation of acetophenone (methyl phenyl ketone=MPK) to methylphenylcarbinol (MPC) according to the reaction scheme specified below is an important industrial step in the preparation of styrene; it is commonly associated with the preparation of propylene oxide by oxidation (oxirane process).

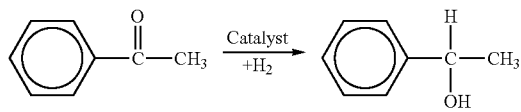

The styrene obtained from MPC by dehydration can be removed easily and is available in a much greater purity than styrene which is obtained by direct dehydrogenation of ethylbenzene. The hydrogenation of acetophenone also opens up an interesting economic route in cases in which acetophenone is obtained as a by-product. The market for acetophenone is restricted to a few specialty applications, while styrene is absorbed readily by the market. In industrial systems, as used, for example, in the oxirane process, the acetophenone can be hydrogenated either in a dispersed phase or in a fixed bed. The catalysts used are typically copper chromites or copper-zinc chromites which exhibit a relatively high MPC selectivity.

It is an object of the invention to even further increase the hydrogenation activity and the selectivity in the hydrogenation of ketones.

It has been found that, surprisingly, this object is achieved with the aid of $SiO_2$-containing copper chromite catalysts.

The invention thus provides a process for hydrogenating ketones, wherein the ketone is fed in a mixture with hydrogen to a catalyst bed which comprises a copper chromite catalyst which has a proportion of $SiO_2$.

It has been found that the catalyst, as a result of the addition of $SiO_2$, attains a higher stability, and the lifetime of the catalyst can therefore be prolonged significantly. Moreover, the copper chromite catalyst used in the process according to the invention exhibits a lower tendency to copper-plate, i.e. the copper surface area available for the catalyzed reaction decreases during the lifetime of the catalyst to a significantly lower degree then in conventionally used copper chromite catalysts. This means that a lower decrease in the activity of the catalyst is achieved over the operating time. Finally, the catalyst used in the process according to the invention exhibits a significantly higher hydrogenation activity in comparison to hydrogenation catalysts used to date for the hydrogenation of ketones. A further advantage of the process according to the invention is that the catalyst used has an increased stability. During use in a reactor, the catalyst therefore decomposes very slowly, so that long operating times are achieved before exchange of the reactor charge is required.

The proportion of $SiO_2$ in the copper chromite catalyst is, based on the oxidized catalyst, preferably from 5 to 15% by weight, especially preferably from 6 to 11% by weight.

The catalyst preferably contains copper in a proportion of from 30 to 40% by weight, especially from 33 to 39% by weight, and chromium in a proportion of from 20 to 30% by weight, preferably from 24 to 29% by weight. The percentage proportions are based on the oxidized form of the catalyst.

The catalyst used in the process according to the invention may also comprise promoter metals in order to influence the properties of the catalyst. The promoter metals are preferably added in a proportion of from 1 to 6% by weight, especially preferably from 1.5 to 5% by weight. The promoter metals are preferably selected from barium and/or manganese.

The catalyst preferably contains, in addition to the abovementioned metals copper and chromium and if appropriate barium and/or manganese, which may be present as the oxide or in a form convertible to an oxide, and the $SiO_2$, further metals only in small amounts. Such metals are, for example, zinc, iron or aluminum. The proportion of these further metals, based on the oxidized catalyst, is in total preferably less than 1% by weight, more preferably less than 0.5% by weight, especially preferably less than 0.4% by weight. The proportion of each individual further metal is, based on the oxidized catalyst, preferably less than 0.2% by weight, especially preferably less than 0.1% by weight. Especially preferably, the proportion of iron, zinc and aluminum is in each case less than 0.1% by weight.

The copper chromite catalysts used in the process according to the invention preferably have a specific surface area of from about 50 to 80 $m^2/g$, in particular of from about 60 to 70 $m^2/g$. The pore volume of the catalysts used is preferably in the range of from 120 to 200 $mm^3/g$, especially preferably from 140 to 180 $mm^3/g$.

The catalyst bed is preferably configured as a fixed bed. The catalysts are generally present in the fixed bed hydrogenation as shaped bodies, for example as tablets. A particularly favorable tablet size is, for instance, 3×3 mm. In principle, the shape of the shaped bodies is not, however, subject to any restrictions, so that other shapes may also be used in addition to an embodiment as a tablet. The shaped bodies generally have a bulk density of from 1400 to 1500 g per liter, a side crushing strength of from about 70 to 105 N and a pore volume of from about 160 to 220 $mm^3/g$.

Catalysts used in the process according to the invention are commercially available. For instance, Süd-Chemie AG supply, under the name "G-22/2", a catalyst which can be used in the process according to the invention. The abovementioned catalyst has been used to date only for the hydrogenation of aldehydes. It has now been found that, surprisingly, this catalyst can also be used for the hydrogenation of ketones, high yields being achieved at a high selectivity, so that the catalyst is also suitable in particular for an industrial scale hydrogenation of ketones.

The catalyst can be prepared by processes known per se. For example, the catalyst used in the process according to the invention can be prepared by precipitation. To this end, aqueous solutions of the metal salts are first prepared, for example in the form of chromates or nitrates, and combined in a controlled manner, so that a precipitate is obtained. $SiO_2$ is added to at least one of the metal salt solutions. The precipitate is removed by customary processes, dried and optionally calcined. For the production of a fixed bed, the catalyst is then pressed in a customary manner to shaped bodies. To this end, the customary assistants may be added, for example graphite as a lubricant. For the production of the tablets, customary tabletting presses may be used.

The process outlined for the preparation of the catalyst should only be interpreted as an example. It is also possible to prepare copper chromite catalysts which contain a proportion of $SiO_2$ by other processes. Such processes are known to those skilled in the art, so that they can effect the preparation of the catalyst easily by customary determination of the preparation parameters.

The process according to the invention is preferably performed with a fixed bed catalyst. To this end, the catalyst is typically introduced into a fixed bed reactor. In order to achieve a uniform flow and temperature distribution, a zone which consists of an inactive material, for example silicon carbide, in which the stream of the reactants is heated to the required reaction temperature and uniform flow is obtained, can be disposed upstream of the catalyst bed. In addition to the catalyst, the fixed bed may also comprise inert materials in a customary manner, in order, for example, to avoid overheating of the reactor and to achieve uniform flow. In addition to the copper chromite catalyst, silicon carbide, for example, may be added to the fixed bed. The inert material is added to the reactor in suitable form, for example in the form of a fine granule, so that the flow conditions in the reactor are not influenced unfavorably.

For the hydrogenation, the ketone and the hydrogen are fed to the reactor, the ketone first being evaporated if appropriate. For the hydrogenation, preference is given to selecting a pressure of more than 10 bar, especially preferably within a range of from 10 to 200 bar, more preferably from 20 to 50 bar. The temperature in the reactor is preferably selected above 70° C., since the reaction rate otherwise decreases greatly. Particular preference is given to selecting the temperature within the range from 70 to 150° C. The feed rate of the ketone (LHSV, liquid hourly space velocity) is preferably selected to be greater than 5, especially preferably between 0.5 and 1.5.

In general, no inert carrier gas is added to the reaction mixture.

The process according to the invention is in principle generally suitable for the reduction of ketones. It has been found that aromatic rings present in addition to the keto group are not hydrogenated. Preference is therefore given in the process according to the invention to using ketones which comprise at least one aromatic group, especially preferably a phenyl group. The process according to the invention is particularly suitable for the reduction of phenyl ketones, particular preference being given to acetophenone. The ketones preferably do not contain any isolated carbon-carbon double bonds.

Figure 2:
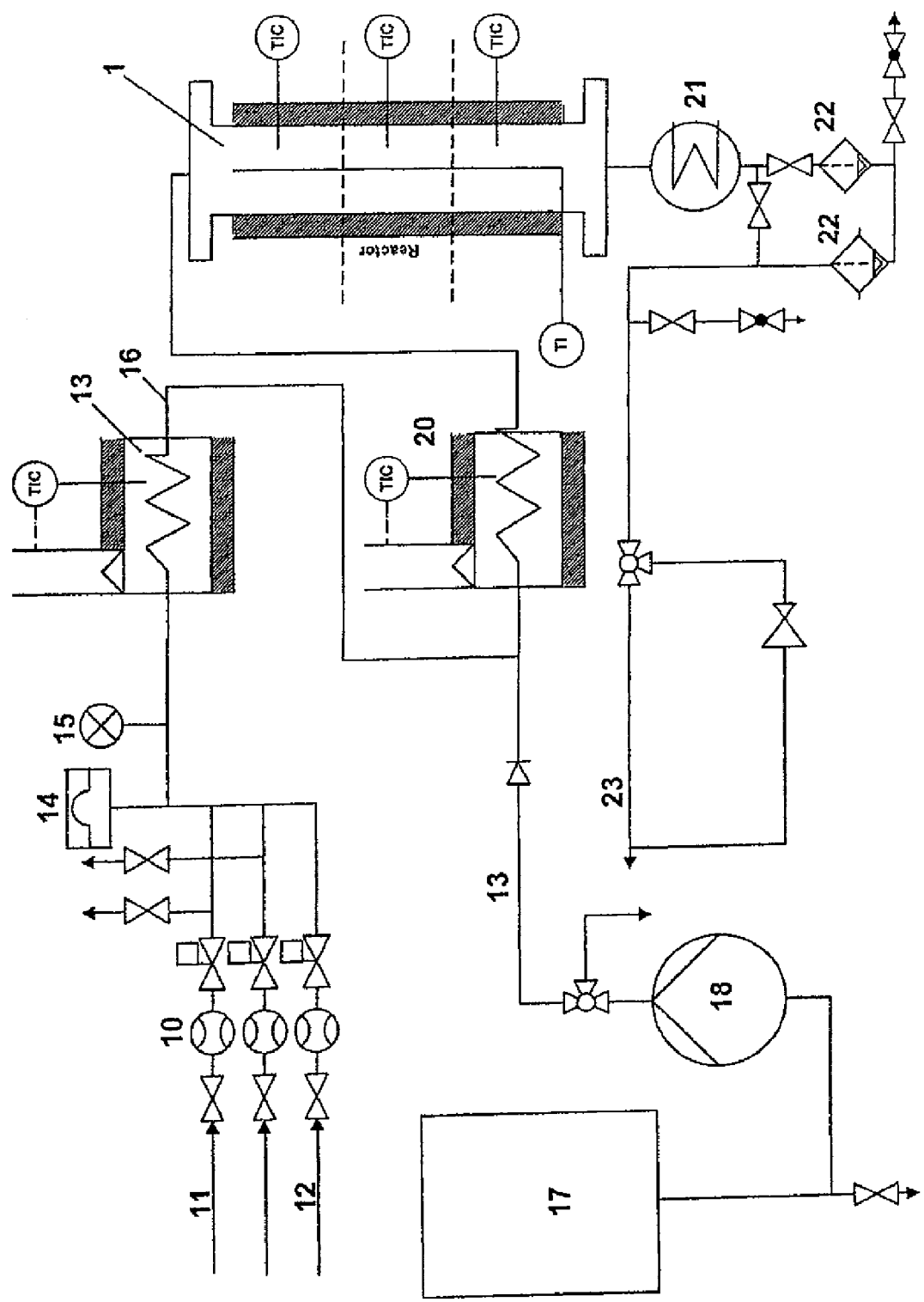
Figure 3:
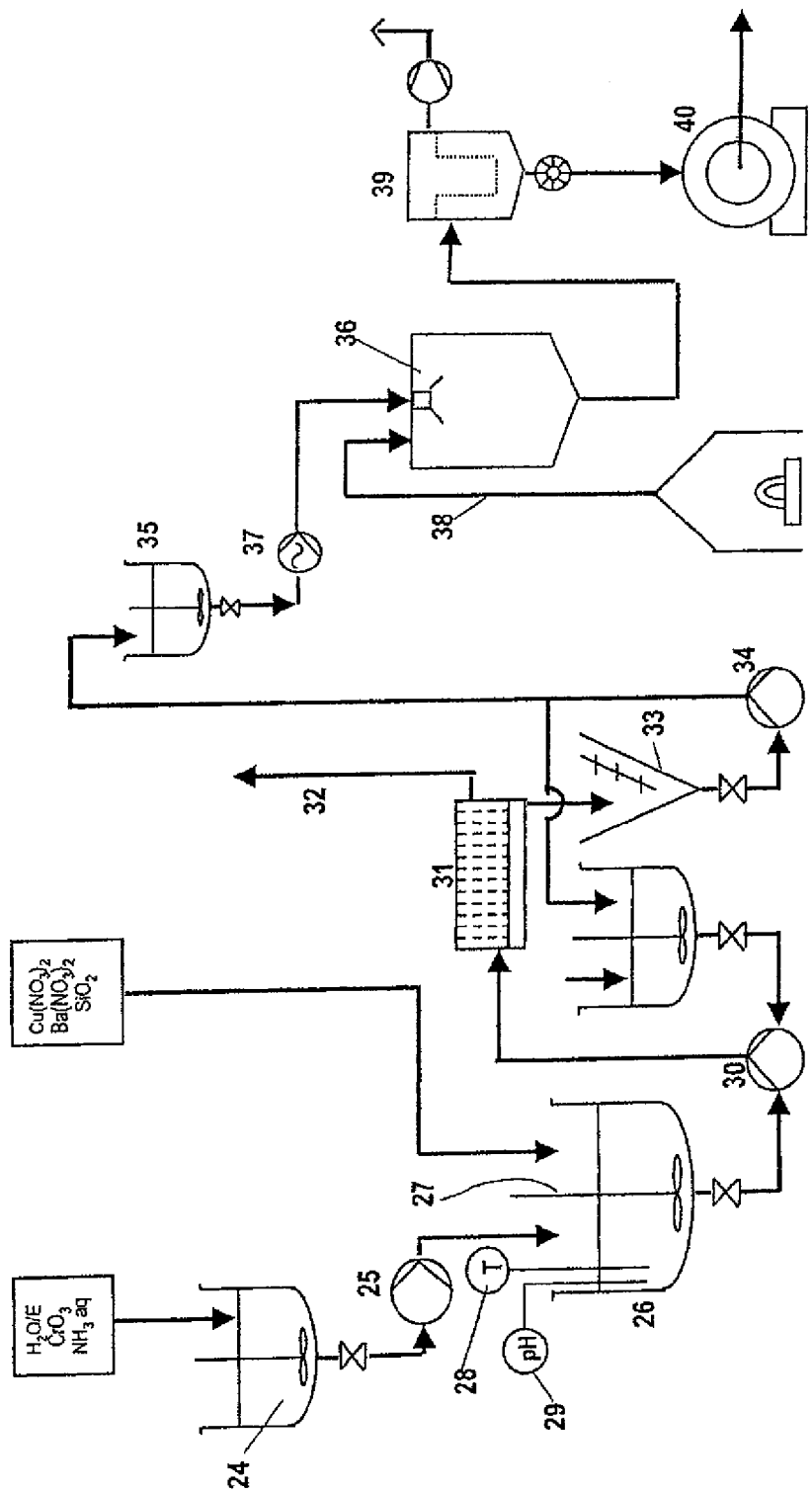
Figure 4:
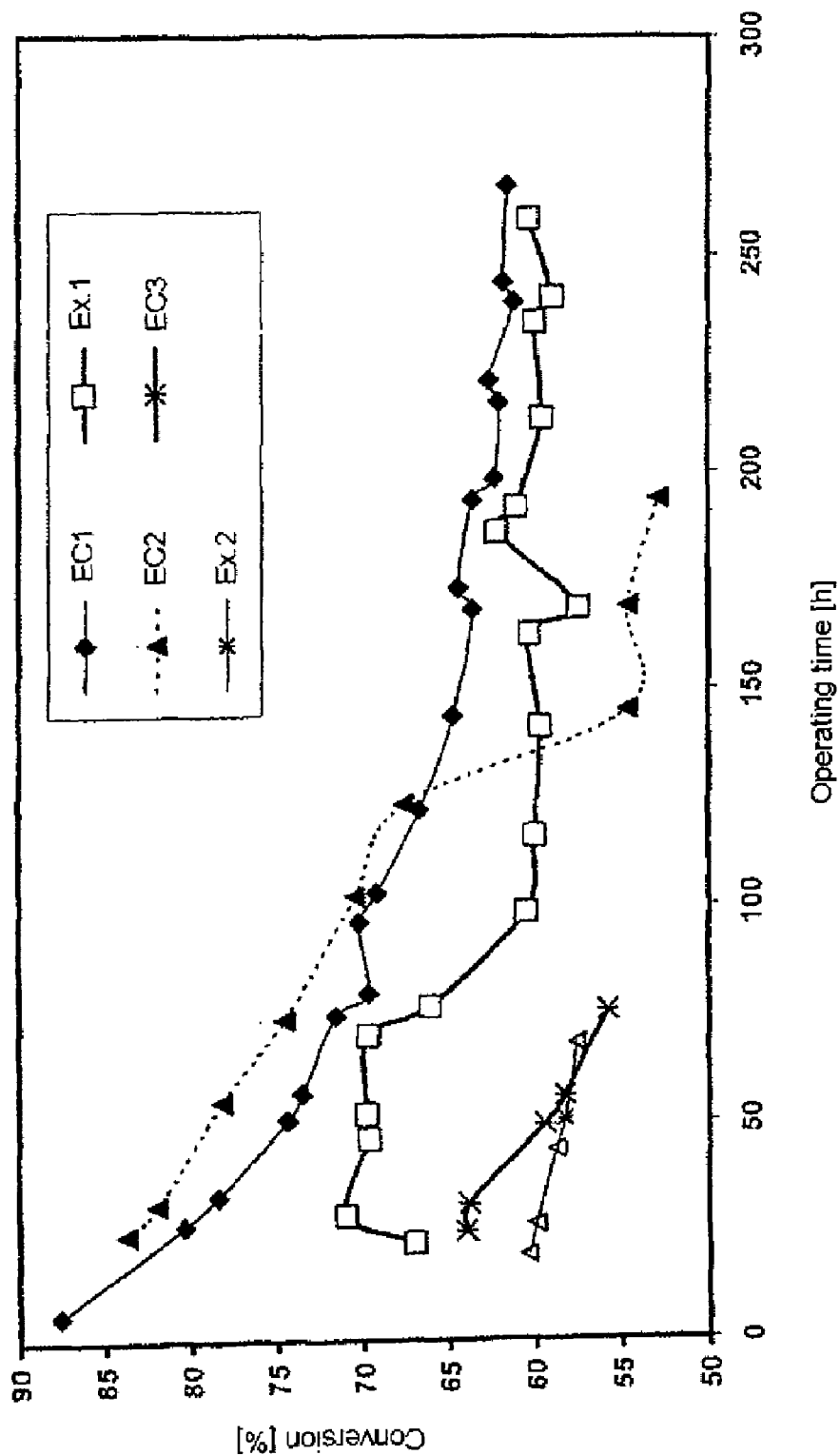
Figure 5:
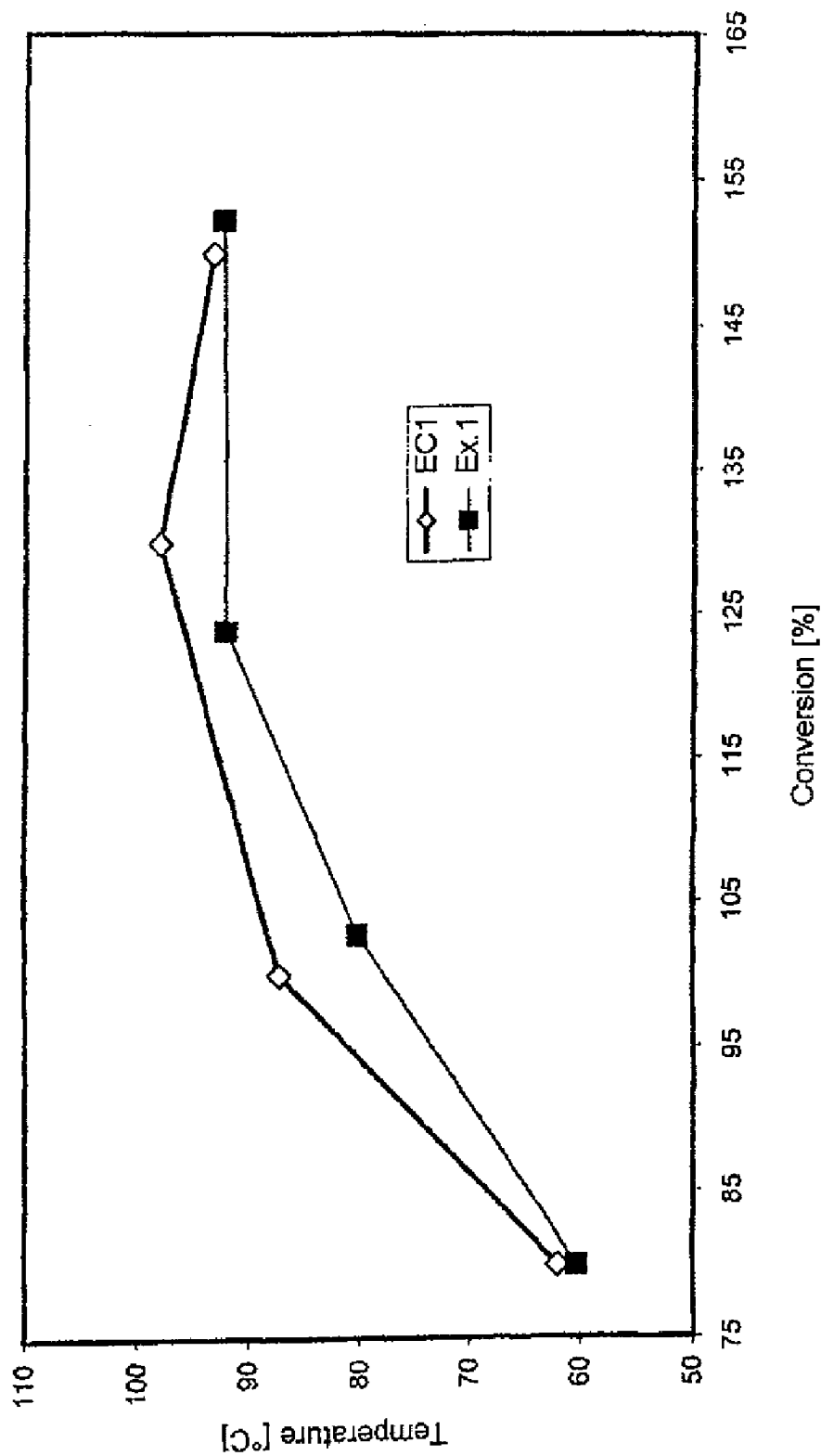
Figure 6:
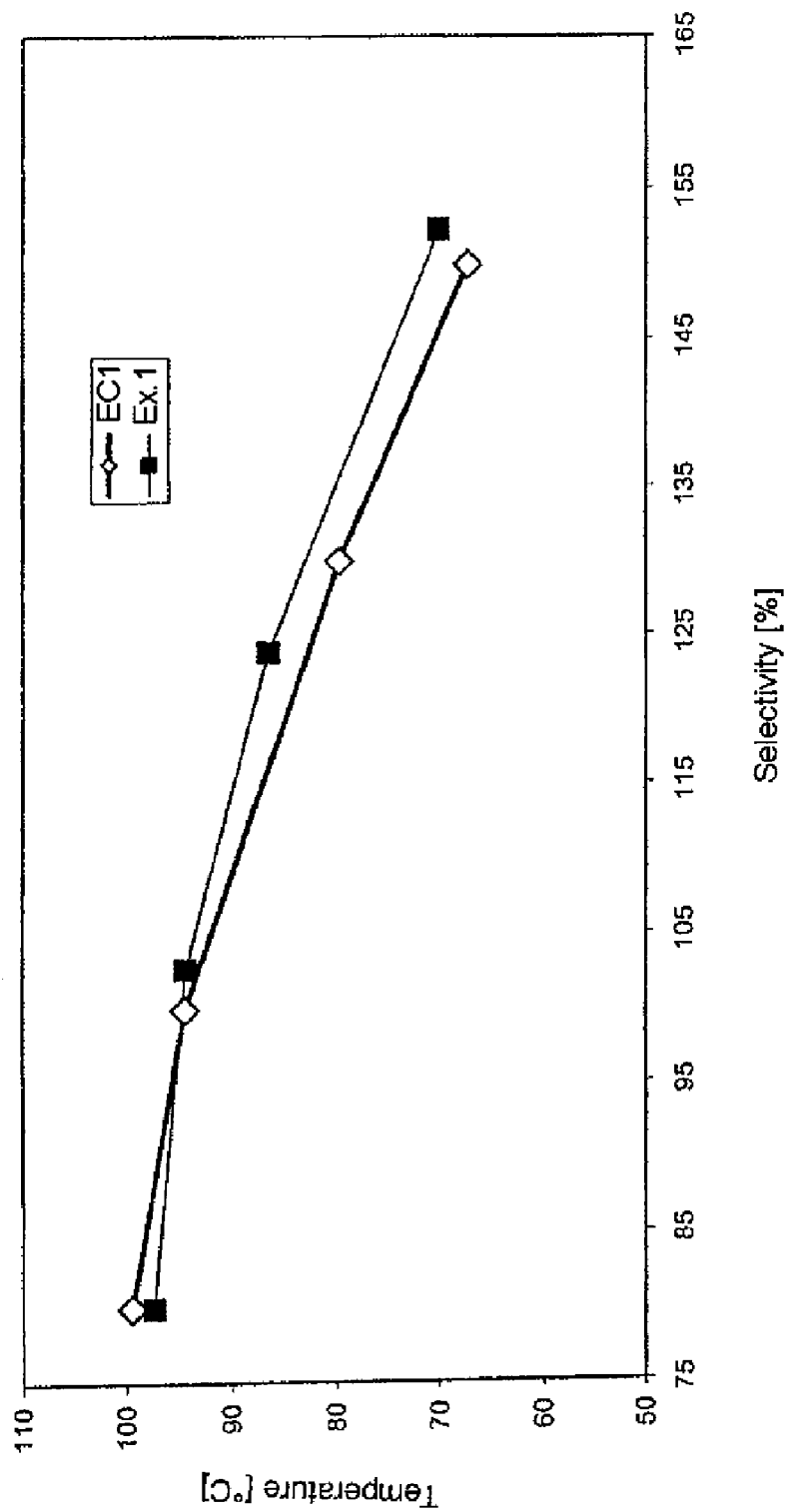
Figure 7:
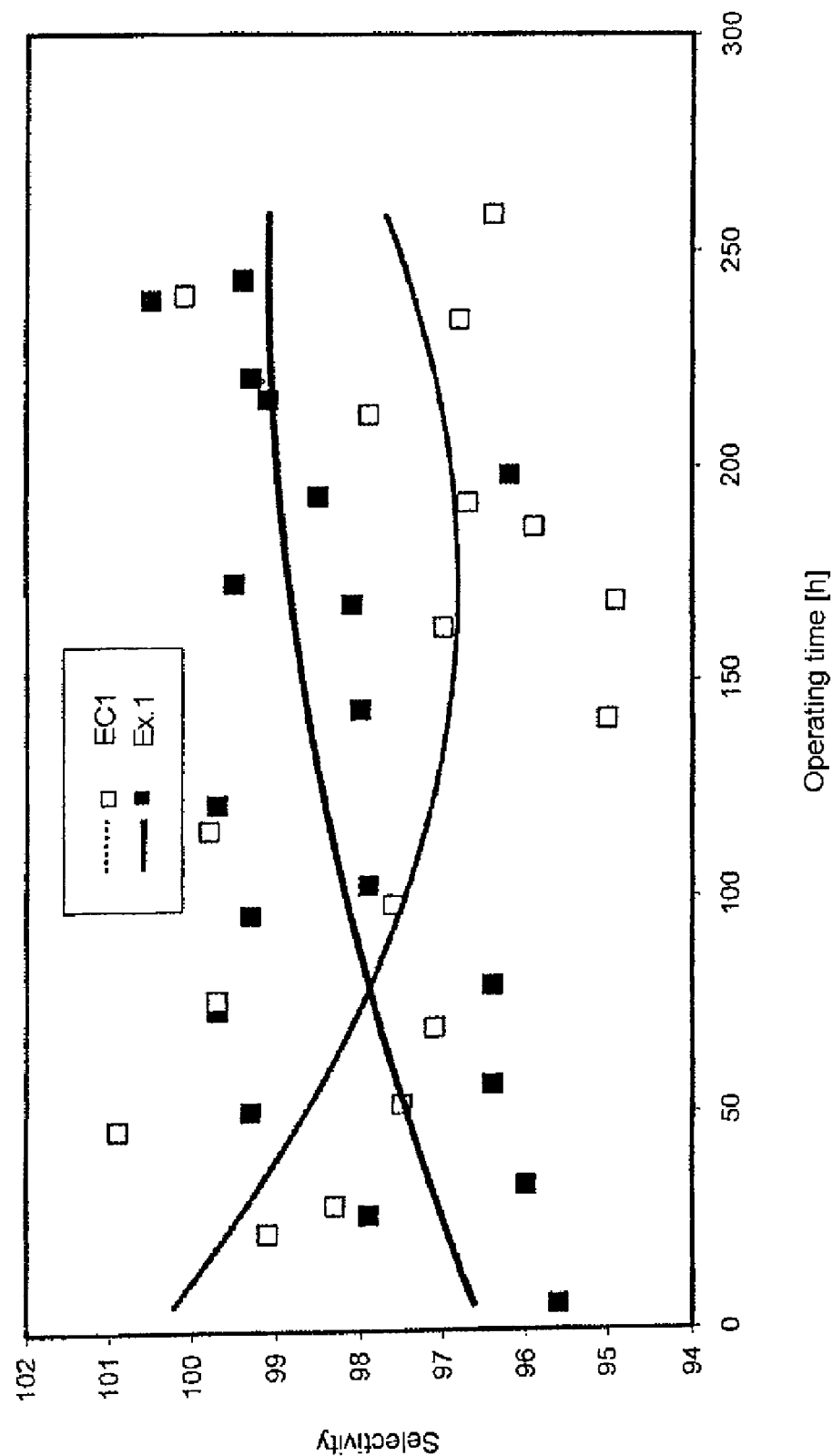
Figure 8:
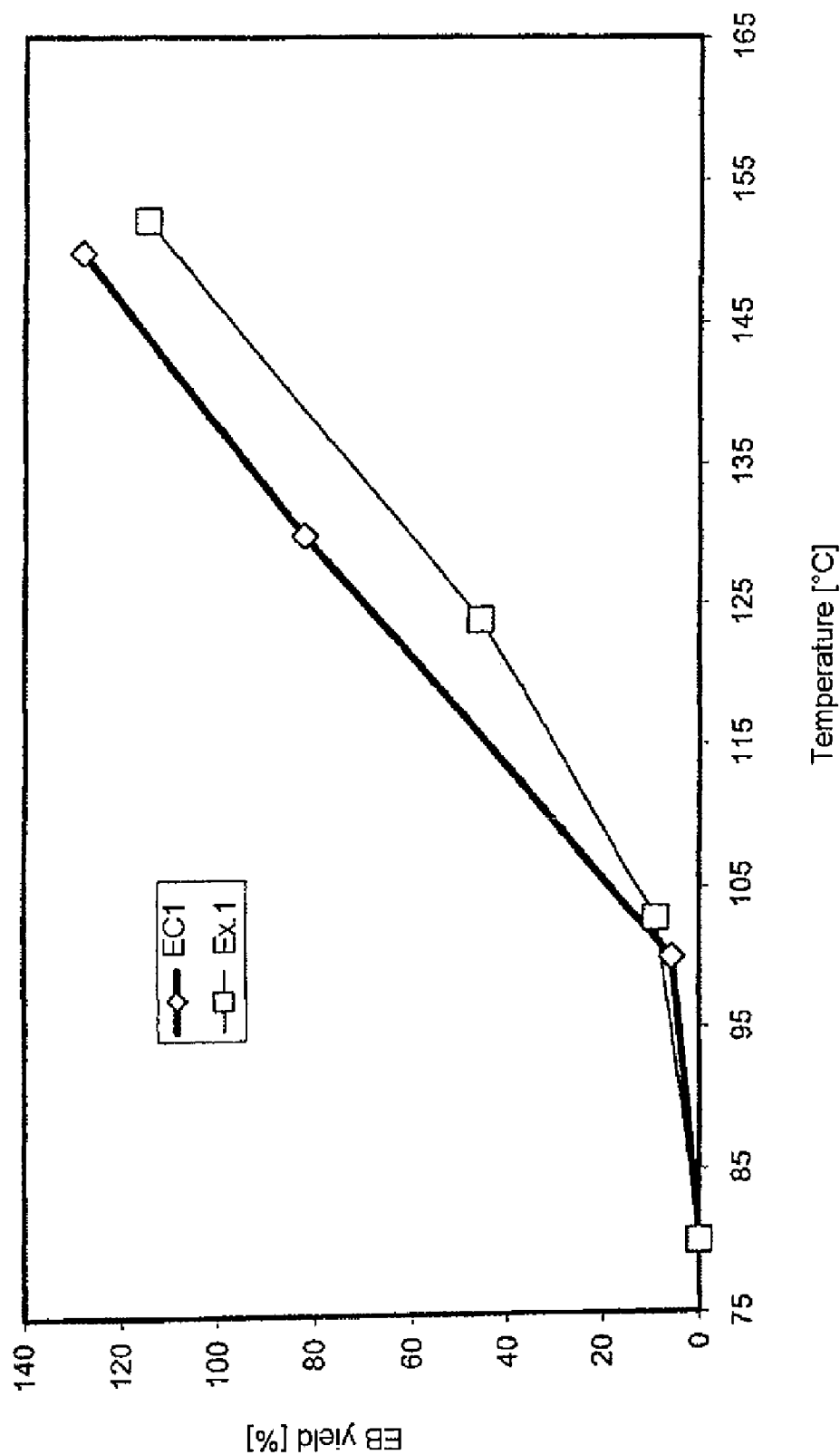

The invention will be illustrated in detail hereinafter with reference to the appended figures. The individual figures show:

FIG. 1: a schematic illustration of a fixed bed reactor as can be used in the process according to the invention;

FIG. 2: a schematic illustration of an apparatus for performing the process according to the invention;

FIG. 3: a schematic illustration of a process for preparing a catalyst as used in the process according to the invention;

FIG. 4: a graph in which the conversion in the hydrogenation of acetophenone is shown as a function of the operating time for various catalysts;

FIG. 5: a graph in which the conversion in the hydrogenation of acetophenone is shown as a function of the temperature for two catalysts;

FIG. 6: a graph in which the selectivity in the reduction of acetophenone is shown as a function of the temperature for two catalysts;

FIG. 7: a graph in which the selectivity for the reduction of acetophenone is shown as a function of the operating time for a comparative catalyst;

FIG. 8: a graph in which the yield of methylbenzene is shown as a function of the temperature for two catalysts.

FIG. 1 shows, by way of example, a section through a fixed bed reactor as can be used in the process according to the invention. In the tubular reactor 1, a fixed bed 3, which comprises the catalyst in the form of tablets which have a diameter of 3 mm and a height of 3 mm, and also silicon carbide with a particle diameter of about 200 μm in a ratio of 1:2, is arranged on a grid 2. Above the fixed bed 3 is arranged a preliminary bed 4 which is formed from silicon carbide particles having a mean diameter of about 200 μm. The reactor is divided into an upper heating zone 5, a middle heating zone 6 and a lower heating zone 7. In the heating zones, the temperature within the reactor 1 is controlled in such a way that approximately isothermal conditions exist over the longitudinal dimension of the reactor 1. The axial temperature distribution in the reactor 1 can be measured by means of a thermoelement 8 through which the heat supply into the heating zones 5, 6 and 7 is controlled by means of a corresponding open-loop control system. At the top of the reactor 1, a reactant stream 9 which comprises hydrogen and gaseous acetophenone is supplied. The reactant stream 9 passes first into the preheating zone 5, where a uniform temperature and a uniform flow profile are established in the preliminary bed 4. The reactant stream 9 then passes through the fixed bed 3, where a reduction of the acetophenone to the methylphenylcarbinol is effected. The product stream is finally conducted out at the lower end of the reactor 1.

In FIG. 1, a reactor with descending product stream is shown by way of example. However, it is also possible to operate the reactor in ascending mode.

FIG. 2 shows a schematic of a structure as can be used to perform the process according to the invention. Mass flow regulators 10 are used to supply hydrogen gas 11 and if appropriate an inert gas 12 to a preheater 13 in which the gases are heated. The gas preparation further includes a safety valve 14 and a manometer 15. The heated gas is supplied via the feed line 16 to the stream of the acetophenone. To this end, the acetophenone is fed from a reservoir vessel 17 by means of a pump 18 via a feed line 19, together with the stream of the reaction gases, to an evaporator 20. The mixture of the reactants is subsequently fed to the reactor 1 in which the reduction of the acetophenone to the methylphenylcarbinol is effected. The product stream is passed to a condenser 21 in which the methylphenylcarbinol is condensed, and then collected in a collecting vessel 22. Hydrogen gas still present in the product stream and any inert gas is removed via the gas outlet 23.

FIG. 3 shows a schematic of the preparation of the catalyst used in the process according to the invention. In a first mixing vessel 24, distilled water is initially charged and $CrO_3$ is dissolved therein. An ammonia solution is then added to the chromic acid solution until the pH is in the range from about 9.5 to 10. If appropriate, the solution can also be diluted with distilled water. The solution heated to 60° C. is passed via a pump 25 to a second mixing vessel 26 in which an aqueous solution of copper nitrate and barium nitrate, to which silicon dioxide has been added, has been initially charged. The mixture is agitated by means of a stirrer 27. The temperature in the second mixing vessel 26 is monitored by means of thermometer 28, and the pH by means of the pH meter 29. At the end of the addition, the pH is from about 6.6 to 7.0. If required, the pH can be adjusted by adding ammonia or nitric acid solution. The suspension is left for another approx. 2 hours in the second mixing vessel 26 to age it, and then fed by means of pump 30 to the filter press 31 in which the filtrate is removed and sent to the wastewater via outlet 32. The filtercake is removed from the filter press 31, homogenized in the mixing vessel 33 and then fed via pump 34 to a reservoir vessel 35. The suspension is finally passed from the reservoir vessel 35 via a pump 37 to a spray dryer 36, and the adhering water is evaporated by feeding hot air 38. The solid constituents are removed in the cyclone 39 and fed to a rotary tube furnace 40 in which a calcination is performed. The calcined powder is then screen-granulated, mixed with graphite, compacted, screen-granulated again and tabletted in a rotary tableting press (not shown).

EXAMPLE 1

Preparation of the Catalyst

In a first mixing vessel, 800 kg of $CrO_3$ are dissolved in 2000 kg of distilled water, and then an ammonia solution which contains 410 kg of $NH_3$ is metered in over one hour. The solution is made up to 7000 l with distilled water and heated to 60° C. The pH of the solution is 9.5 to 10. In a second mixing vessel, a copper nitrate and barium nitrate solution which contains 640 kg of copper and 150 kg of barium is prepared. The solution is diluted to 5800 l with distilled water and heated to 60° C. The pH of this solution is from 2 to 2.5. 176 kg of $SiO_2$ are also added to this solution. The ammonium chromate solution prepared in the first mixing vessel is metered into the second mixing vessel at 60° C. over 120 minutes. The pH of the mixture rises at the end of the precipitation to from 6.6 to 7.0. If required, the pH can be adjusted by adding ammonia or nitric acid solution. The precipitate is aged for another two hours and then the suspension is filtered with the aid of a filter press. The filtercake is homogenized in a mixing vessel and then spray-dried and calcined in a rotary tube furnace. The calcined product has a BET surface area of 70 m²/g, a copper content of 38%, a chromium content of 25% and an $SiO_2$ content of 10%. The ignition loss at 1000° C. is 6%. The calcined powder is screen-granulated and mixed with 2% graphite. The mixture is compacted, screen-granulated again and tabletted to 3×3 mm with a rotary tableting press.

EXAMPLE 2

In the same way as described in example 1, a catalyst which also comprised manganese in addition to barium as a promoter was prepared. The manganese was introduced by replacing some of the barium nitrate with manganese nitrate. The catalyst contained 33.6% copper, 29.5% chromium, 1.9% barium, 2.1% manganese and 9.4% $SiO_2$. The ignition loss at 1000° C. was determined to be 3.9%.

The chemical composition and the physical properties of the inventive catalysts (example 1 and example 2) and some commercial comparative catalysts (T-4492=CE 1, T-2130=CE 2 and T-4489=CE 3) (manufacturer: Süd-Chemie AG) are specified in table I below.

TABLE I

| Product<br>Particle form<br>Particle size | | Ex. 1<br>Tablets<br>3 × 3 mm | Ex. 2<br>Tablets<br>3 × 3 mm | CE 1<br>Tablets<br>3 × 3 mm | CE 2<br>Tablets<br>3 × 3 mm | CE 3<br>Tablets<br>3 × 3 mm |
|---|---|---|---|---|---|---|
| Chem.<br>composition | Copper (without IL) [%] | 38.4 | 33.6 | 34.5 | 25.8 | 44.5 |
| | Zinc (without IL) [%] | — | — | 43.1 | 53.7 | — |
| | Chromium (without IL) [%] | 24.8 | 29.5 | — | — | — |
| | Barium (without IL) [%] | 6.1 | 1.9 | — | — | — |
| | Aluminum (without IL) [%] | — | — | — | — | 18.0 |
| | Manganese (without IL) [%] | — | 2.1 | 2.2 | — | 6.6 |
| | $SiO_2$ (without IL) [%] | 10.0 | 9.4 | — | — | — |
| Physical<br>properties | IL (1000° C.)[1] [%] | 6.2 | 3.9 | 9.6 | 7.7 | 5.6 |
| | Specific surface area[2] [m²/g] | 74 | 58 | 70 | 61 | 46.8 |
| | Bulk density [g/l] | 1450 | 1480 | 1420 | 1450 | 1470 |
| | Side crushing strength[3] [m²/g] | 102 | 87 | 83 | 72 | 93 |
| | Pore volume[4] [mm³/g] | 176 | 147 | 210 | 165 | 167 |
| | Pore radius distribution[5] [mm³/g] | | | | | |
| | 7500-875 nm | 0.0 | 1.9 | 0.9 | 0.5 | 0.0 |
| | 875-40 nm | 29.9 | 11.8 | 18.3 | 6.2 | 4.6 |
| | 40-7 nm | 113.7 | 114.6 | 167.4 | 62.3 | 135.3 |
| | 7-3.7 nm | 32.8 | 19.0 | 23.3 | 31.0 | 27.5 |

[1] IL = Ignition loss
[2] BET surface area to DIN 66131
[3] Side crushing strength to DIN EN 1094-5
[4] Pore volume to DIN 66133 (by means of mercury)
[5] Pore radius distribution to DIN 6133

EXAMPLE 3

Hydrogenation of Acetophenone

The catalysts detailed in table 1 were evaluated in a test setup as shown schematically in FIGS. 1 and 2. The inert gas used was nitrogen.

The catalysts present in their oxidized form were each introduced into the reactor together with SiC in a ratio of 1:2 and then reduced first with reducing gas (2% $H_2$ in 98% $N_2$) for 16 hours and then with pure hydrogen for another 3 hours at a flow rate of about 35 l (STP)/h. The temperature in reactor 1 was adjusted to 175 or 200° C. The temperature in the preheater 13 and in the evaporator 20 was in each case 150° C. The condenser 21 was cooled with tap water. After the reduction of the oxidic catalyst, the apparatus was flushed with nitrogen before the introduction of the methyl ethyl ketone. The pressure was adjusted to 5 bar of nitrogen until the start of the actual test. The total weight of the catalyst was calculated at 0.04 liter×bulk density.

After the catalyst activation had ended, the reactor 1 was depressurized and purged with hydrogen for a few minutes. The flow rate of the hydrogen was 4.8 l (STP)/$H_2$ (GHSV=120). The flow rate of the methyl ethyl ketone was 32.2 l (STP)/h (LHSV=0.8). The pressure in the reactor was adjusted to 25 bar.

The hydrogen pressure was then increased to 35 bar, and the temperature in the preheater 13, evaporator 20, in the reactor feedline and in the three zones 5, 6, 7 of the reactor 1 was adjusted to 80° C. The temperature profile of the catalyst bed was measured every 10 minutes. After a reaction time of about 3 hours, the collecting vessel 22 for the products was removed, emptied and attached again for the sampling.

The samples were taken twice each day (in the morning and in the afternoon). To this end, a temperature profile of the catalyst bed was first recorded. The air pressure, the room temperature, the gas volume, the mass of the starting material consumed, the mass of the products formed and the time were likewise recorded. The collecting vessel 22 was emptied and then the product was collected over about 1 hour. The collected sample was then transferred to a 30 ml screwcap bottle. The bottles were labeled with the sample number, the date and the process temperature.

The liquid samples were analyzed by gas chromatography (GC) using a "Siemens Sichromat 3A" gas chromatograph. The column (30 m long, internal diameter 0.32 mm; df=0.50 µm) contained CP wax 52 CB. The carrier gas used was nitrogen with a pressure of 0.5 bar, the combustion gas air at 2 bar and hydrogen at 2 bar. The split was 135 ml/min. The septum was purged at 13 ml/min. The temperature of the injector was 250° C., that of the detector (FID) 330° C. The amount of sample was in each case 0.1 µl. The experiment time was 60 min, the temperature 50° C. (0 min) to 250° C. (30 min). The following peaks were identified:

1. N-Decane (int. standard)
2. Ethylbenzene (EB)
3. Styrene
4. Benzaldehyde
5. Acetophenone
6. 1-Phenylethanol
7. Benzyl alcohol
8. 2-Phenylethanol The parameters recorded for the samplings and the results of the gas chromatography analyses were entered into a spreadsheet in order to calculate the MPK conversion, the MPC yield, the MPC selectivity and the EB yield.

Evaluation

Definitions (all percentages in % by weight)

$$\text{MPK conversion} = \left[\left(1 - \frac{\text{MPK [\%] (sample)}}{\text{MPK [\%] (use)}}\right)\right] \times 100$$

$$\text{MPC yield} = \frac{\text{MPC [\%] (sample)} \times \text{liquid (out) [g/h]} -}{\text{MPK [\%] (in)} \times \text{use (in) [g/h]}} \times 100$$

$$\text{MPC selectivity} = \frac{\text{MPC yield}}{\text{MPK conversion}} \times 100$$

$$\text{EB yield} = \frac{\text{EB [\%] (products)} - \text{EB [\%] (use)}}{\text{EB [\%] (use)}} \times 100$$

EB yield at higher temperatures ($xy°$ C.) based on EB yield at 80° C.

$$\frac{\text{EB yield [\%] } (xy° \text{ C.}) - \text{EB yield [\%] } (80° \text{ C.})}{\text{EB yield [\%] } (80° \text{ C.})}.$$

The test results are reported in tables II to VI and shown graphically in FIGS. 4 to 8.

TABLE II

Results with the catalyst of example 1

| Operating time [h] | Temperature | MPK conversion [%] | MPC selectivity [%] | Styrene [%] | Benzaldehyde [%] | Ethylbenzene production [%] |
|---|---|---|---|---|---|---|
| 22.50 | | 67.4 | 99.1 | 0.08 | 0.08 | 15.8* |
| 28.75 | | 71.0 | 98.3 | 0.00 | 0.07 | 14.5* |
| 46.50 | | 69.7 | 100.7 | 0.00 | 0.08 | 17.6* |
| 52.20 | | 69.8 | 97.5 | 0.00 | 0.07 | 14.8* |
| 70.20 | | 69.7 | 100.1 | 0.00 | 0.08 | 15.5* |
| 76.70 | | 66.1 | 99.7 | 0.00 | 0.08 | 16.2 |
| 98.50 | | 60.5 | 97.6 | 0.04 | 0.09 | 14.8* |
| 116.00 | | 60.0 | 101.9 | 0.03 | 0.08 | 17.4* |
| 141.25 | | 59.7 | 97.0 | 0.00 | 0.08 | 16.7 |
| 162.50 | | 60.3 | 97.0 | 0.00 | 0.08 | 16.4* |
| 168.50 | | 57.5 | 94.9 | 0.04 | 0.09 | 15.0* |
| 186.00 | | 62.2 | 95.9 | 0.00 | 0.08 | 15.7* |
| 191.75 | | 60.8 | 96.7 | 0.00 | 0.08 | 16.5* |
| 212.75 | | 59.6 | 97.9 | 0.00 | 0.08 | 17.8* |
| 234.75 | | 60.0 | 96.8 | 0.00 | 0.08 | 16.1 |
| 240.50 | | 59 | 100.1 | 0.00 | 0.08 | 18.8* |
| 258.50 | | 60.3 | 96.4 | 0.00 | 0.08 | 15.0* |
| 306.00 | 100 | 80.2 | 94.3 | — | — | 7.8** |
| 332.25 | 130 | 92.1 | 86.5 | — | — | 59.8** |
| 353.75 | 150 | 92.3 | 70.1 | — | — | 109.1** |
| 376.75 | 80 | 47.5 | 92.1 | 0.05 | 0.1 | 17.0* |

*by hydrogenation of styrene (conversion of styrene = ethylbenzene yield)
**by hydrogenolysis of MPK (ethylbenzene formation from styrene is defined as % by weight of ethylbenzene at the outlet at 80° C.)

TABLE III

Results with the catalyst of example 2

| Operating time [h] | MPK conversion [%] | MPC selectivity [%] | Styrene [%] | Benzaldehyde [%] | Ethylbenzene yield [%] |
|---|---|---|---|---|---|
| 19.5 | 60.4 | 94.3 | 0 | 0.07 | 14.1* |
| 26.5 | 59.9 | 93.3 | 0 | 0.06 | 13.8* |
| 43.75 | 58.8 | 95 | 0 | 0.06 | 14.7* |
| 50.75 | 58.3 | 97.3 | 0 | 0.06 | 14.1* |
| 68 | 57.6 | 95.5 | 0 | 0.06 | 15.4* |

*by hydrogenation of styrene (conversion of styrene = ethylbenzene yield)

TABLE IV

Results with the catalyst of CE 1

| Operating time [h] | Temperature | MPK conversion [%] | MPC selectivity [%] | Styrene [%] | Benzaldehyde [%] | Ethylbenzene yield [%] |
|---|---|---|---|---|---|---|
| 6.0 | | 86.6 | 95.6 | 0.05 | 0.11 | 19.7* |
| 26.25 | | 80.4 | 97.9 | 0 | 0.07 | 16.5* |
| 33.25 | | 78.4 | 96.0 | 0 | 0.07 | 15.2* |
| 50.75 | | 74.4 | 99.3 | 0 | 0.07 | 16.4* |
| 56.75 | | 73.6 | 96.4 | 0 | 0.07 | 15.7 |
| 74.50 | | 71.6 | 99.7 | 0 | 0.07 | 17.3* |
| 79.75 | | 69.7 | 96.4 | 0 | 0.07 | 13.1* |
| 96.25 | | 70.2 | 99.3 | 0 | 0.07 | 16.7* |
| 103.00 | | 69.2 | 97.9 | 0 | 0.07 | 14.3* |
| 122.00 | | 66.7 | 100.3 | 0 | 0.08 | 17.6* |
| 143.73 | | 64.7 | 98.0 | 0 | 0.08 | 14.7* |
| 168.06 | | 63.7 | 98.1 | 0 | 0.07 | 16.2* |
| 173.06 | | 64.4 | 99.5 | 0 | 0.08 | 17.6* |
| 193.30 | | 63.6 | 98.5 | 0 | 0.07 | 16.0* |
| 198.30 | | 62.3 | 96.2 | 0 | 0.08 | 15.9* |
| 216.30 | | 62.1 | 99.1 | 0 | 0.07 | 16.6* |
| 221.30 | | 62.6 | 99.3 | 0 | 0.08 | 14.9* |
| 239.30 | | 61.2 | 100.5 | 0 | 0.08 | 16.8* |
| 243.80 | | 61.8 | 99.4 | 0 | 0.08 | 17.4* |
| 266.05 | | 61.6 | 99.6 | 0 | 0.08 | 17.6* |
| 309.80 | 100 | 87.3 | 94.4 | — | — | 5.6** |
| 337.55 | 130 | 98 | 79.7 | — | — | 82.3** |
| 358.55 | 150 | 93.2 | 67.3 | — | — | 128.0** |
| 378.05 | 80 | 53.6 | 93.4 | 0.05 | 0.1 | 22.6* |

*by hydrogenation of styrene (conversion of styrene = ethylbenzene yield)
**by hydrogenolysis of MPK (ethylbenzene formation from styrene is defined as % by weight of ethylbenzene at the outlet at 80° C.)

TABLE V

Results with the catalyst of CE 2 (T-2130)

| Operating time [h] | MPK conversion [%] | MPC selectivity [%] | Styrene [%] | Benzaldehyde [%] | Ethylbenzene yield [%] |
|---|---|---|---|---|---|
| 24.5 | 83.8 | 100.1 | 0 | 0.06 | 17.6* |
| 31.25 | 82.0 | 97.4 | 0 | 0.06 | 18.0* |
| 49.00 | 81.8 | 98.3 | 0 | 0.06 | 18.8* |
| 55.00 | 78.2 | 99.3 | 0 | 0.06 | 19.2* |
| 73.80 | 74.6 | 97.2 | 0 | 0.06 | 16.3* |
| 102.30 | 70.5 | 95.5 | 0 | 0.06 | 14.1* |
| 123.40 | 67.6 | 98.1 | 0 | 0.06 | 15.9* |
| 144.90 | 54.6 | 94.4 | 0 | 0.06 | 15.2* |
| 168.70 | 54.6 | 96.0 | 0 | 0.06 | 15.9* |
| 193.40 | 52.9 | 95.1 | 0 | 0.06 | 15.4* |

*by hydrogenation of styrene (conversion of styrene = ethylbenzene yield)

TABLE VI

Results with the catalyst of CE 3 (T-4489)

| Operating time [h] | MPK conversion [%] | MPC selectivity [%] | Styrene [%] | Benzaldehyde [%] | Ethylbenzene yield [%] |
|---|---|---|---|---|---|
| 25.0 | 64 | 99.1 | 0 | 0.07 | 19.1* |
| 31.3 | 63.8 | 95.0 | 0 | 0.07 | 15.4* |
| 49.5 | 59.4 | 98.8 | 0 | 0.07 | 16.8* |
| 56.0 | 58.3 | 97.8 | 0 | 0.07 | 16.2* |
| 75.5 | 55.8 | 96.1 | 0 | 0.07 | 15.5* |

*by hydrogenation of styrene (conversion of styrene = ethylbenzene yield)

FIG. 4 shows a graph in which the conversion of acetophenone is shown as a function of the operating time. At the start of the experiment, the catalysts from comparative examples 1 and 2 show a high conversion, which decreases continuously with increasing operating time in the case of catalyst CE 1. Catalyst CE 2 initially exhibits a similar profile to catalyst CE 1, except that a sharp fall in the conversion was observed after an operating time of 140 hours. After the experiment time of 200 hours had expired, the catalysts were removed from the reactor, which showed that more than 50% of the tablets produced from catalyst CE 2 had fallen apart and were present only as powder. The catalyst from example 1 used in the process according to the invention exhibited a somewhat lower conversion than the catalysts CE 1 and CE 2 at the start of the experiment time. However, with increasing operating time, the conversion approached the conversion as was observed with catalyst CE 1.

The conversions for catalyst CE 3 and the catalyst from example 2 were comparatively low at the start of the experiment in comparison to the other catalysts tested, so that the test was terminated after approx. 70 hours.

In the figures which follow, only the catalysts from example 1 and comparative example 1 are taken into account, since they exhibited the best performance in relation to the conversion as a function of the operating time.

FIG. 5 shows the conversion as a function of the temperature. It can be seen that a conversion of approx. 60% is observed both for the catalyst CE 1 and for the catalyst from example 1 at temperatures in the region of 80° C. The conversion rate for the acetophenone increases with increasing temperature until it approximates to a plateau at approx. 130° C. The two curves show an approximately parallel profile.

FIG. 6 shows the selectivity in relation to methylphenylcarbinol as a function of the temperature. It is found that the catalyst from CE 1 has a slightly higher selectivity at lower temperatures than the catalyst from example 1 used in the process according to the invention. With increasing temperature, the selectivity for the catalyst from CE 1 decreases to a greater degree. At temperatures above approx. 120° C., the catalyst from example 1 exhibits a better selectivity in comparison to catalyst CE 1.

FIG. 7 reports the selectivity as a function of the operating time for the catalyst from example 1 and CE 1. It is found that the selectivity remains approximately constant over the operating time for the catalyst from example 1. For the catalyst from CE 1, the selectivity falls slightly with increasing operating time.

FIG. 8 finally shows the yield of ethylbenzene as an undesired by-product as a function of the temperature. While both catalysts generate only small amounts of ethylbenzene at low temperatures, a significantly lower proportion of ethylbenzene by-product is observed at higher temperatures in the case of the catalyst from example 1 used in the process according to the invention.

Overall, it is evident that, under conditions as used for the industrial use, the catalyst used in the process according to the invention gives rise to a better selectivity and hence a lower proportion of undesired by-products than the catalyst CE 1 employed as the comparative example.

Side Crushing Strength

The catalyst tablets from example 1 and comparative example 1 were each tested for their side crushing strength (DIN EN 1094-5) before and after the hydrogenation performed in example 3. The results are compiled in table VII.

TABLE VII

Testing of the side crushing strength

| Product | | | Example 1 Tablets | | Comp. Ex. 1 Tablets | |
|---|---|---|---|---|---|---|
| Particle form | | | | | | |
| Particle size | | | 3 × 3 mm | | 3 × 3 mm | |
| Type of tablets | | | Before test | After test | Before test | After test |
| Side crushing strength | Average | [N] | 102 | 106 | 83 | 41 |
| | Min. | [N] | 28 | 48 | 46 | 26 |
| | Max | [N] | 197 | 189 | 147 | 69 |

The catalyst from example 1 used in accordance with the invention, even after the test, i.e. after the hydrogenation of acetophenone, exhibits virtually no change in the side crushing strength, or even a slight increase is observed. The catalyst from comparative example 1, in contrast, exhibits a deterioration in the side crushing strength. In the case of industrial use, this means that the decomposition of the catalyst from example 1 does not occur until significantly later than in the case of the catalyst from comparative example 1. The backpressure in the reactor thus rises significantly more slowly over time. It is possible to achieve significantly longer operating times, i.e. the catalyst only has to be exchanged at significantly greater time intervals.

| Reference numeral list | |
|---|---|
| 1 | Reactor |
| 2 | Grid |
| 3 | Fixed bed |
| 4 | Preliminary bed |
| 5 | Upper heating zone |
| 6 | Middle heating zone |
| 7 | Lower heating zone |
| 8 | Thermoelement |
| 9 | Product stream |
| 10 | Mass flow regulator |
| 11 | Hydrogen gas |
| 12 | Inert gas |
| 13 | Preheater |
| 14 | Safety valve |
| 15 | Manometer |
| 16 | Feed line |
| 17 | Reservoir vessel |
| 18 | Pump |
| 19 | Feed line |
| 20 | Evaporator |
| 21 | Condenser |
| 22 | Collecting vessel |
| 23 | Gas outlet |
| 24 | First mixing vessel |
| 25 | Pump |
| 26 | Second mixing vessel |
| 27 | Stirrer |
| 28 | Thermometer |
| 29 | pH meter |
| 30 | Pump |
| 31 | Filter press |
| 32 | Outlet |
| 33 | Mixing vessel |
| 34 | Pump |
| 35 | Reservoir vessel |
| 36 | Spray dryer |
| 37 | Pump |
| 38 | Hot air feed |
| 39 | Cyclone |
| 40 | Rotary tube furnace |

The invention claimed is:

1. A process for hydrogenating phenyl ketones, comprising feeding the ketone in a mixture with hydrogen to a catalyst bed containing catalysts which comprise a copper chromite catalyst which has a proportion of $SiO_2$, wherein the catalyst comprises copper in a proportion of 30 to 40% by weight, and chromium in a proportion of 20 to 30% by weight, and the proportion of $SiO_2$ is within the range from 5 to 15% by weight, base on the oxidized form of the catalyst, and wherein the catalyst is provided by preparing and combining aqueous solution of metal salts, so that a precipitate is obtained, wherein $SiO_2$ is added to at least one of the metal salt solutions.

2. The process as claimed in claim 1 wherein the copper chromite catalyst, based on the oxidized catalyst, contains promoter metals in a proportion of from 1 to 6% by weight.

3. The process as claimed in claim 2 wherein the promoter metals are selected form barium and/or manganese.

4. The process as claimed in claim 1, wherein the hydrogenation is performed within a pressure range of from 10 to 200 bar, at a temperature of more than 70° C. and at an LHSV in the range of from 0.5 to 1.5.

5. The process as claimed in claim 1 wherein no inert carrier gas is added to the hydrogen and to the ketone.

6. The process as claimed in claim 1 wherein the phenyl ketone is acetophenone.

7. A process for hydrogenating phenyl ketones, comprising feeding the ketone in a mixture with hydrogen to a catalyst bed containing catalysts which comprise a copper chromite catalyst which has a proportion of $SiO_2$, wherein the catalyst is provided by preparing and combining aqueous solutions of metal salts, so that a precipitate is obtained, wherein $SiO_2$ is added to at least one of the metal salt solutions.

8. The process as claimed in claim 1, wherein the copper chromite catalyst has a specific surface area of from about 50 to 80 $m^2/g$.

9. The process as claimed in claim 1, wherein the catalyst bed is configured as a fixed bed.

10. The process as claimed in claim 7 wherein the copper chromite catalyst has a specific surface area of from about 50 to 80 $m^2/g$.

11. The process as claimed in claim 7 wherein the catalyst bed is configured as a fixed bed.

* * * * *